US00PP13801P29

(12) United States Plant Patent
Vandenberg

(10) Patent No.: US PP13,801 P2
(45) Date of Patent: May 13, 2003

(54) CHRYSANTHEMUM PLANT NAMED 'SWEET YOSTACY'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/094,269

(22) Filed: Mar. 8, 2002

(51) Int. Cl.[7] ..... A01H 5/00

(52) U.S. Cl. ..... Plt./286

(58) Field of Search ..... Plt./286

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Sweet Yostacy', characterized by its upright and mounded plant habit; freely branching habit; uniform and freely flowering habit; daisy-type inflorescences; pale yellow-colored ray florets with pink-colored apices; and natural season flowering in early October in the Northern Hemisphere.

1 Drawing Sheet

BOTANICAL CLASSIFICATION/CULTIVAR DESIGNATION

*Chrysanthemum×morifolium* cultivar Sweet Yostacy.

BACKGROUND OF THE INVENTION

The present invention relates to a new and distinct cultivar of Chrysanthemum plant, botanically known as *Chrysanthemum×morifolium*, commercially known as a garden-type Chrysanthemum and hereinafter referred to by the name 'Sweet Yostacy'.

The new cultivar is a product of a mutation induction breeding program conducted by the Inventor in Salinas, Calif. and Fort Myers, Fla. The objective of the program is to create new garden-type Chrysanthemum cultivars having inflorescences with desirable inflorescence forms, attractive floret colors and good garden performance.

The new Chrysanthemum originated by exposing unrooted cuttings of the Chrysanthemum cultivar Stacy, disclosed in U.S. Plant Pat. No. 11,852, to X-ray radiation in March, 1997 in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The new Chrysanthemum was discovered and selected by the Inventor as a single flowering plant within this population in October, 1997. The selection of this plant was based on its desirable inflorescence form, attractive ray floret color and good garden performance.

Asexual reproduction of the new cultivar by terminal cuttings taken in a controlled environment in Salinas, Calif. since December, 1997, has shown that the unique features of this new Chrysanthemum are stable and reproduced true to type in successive generations.

SUMMARY OF THE INVENTION

The cultivar Sweet Yostacy has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sweet Yostacy'. These characteristics in combination distinguish 'Sweet Yostacy' as a new and distinct cultivar:

1. Upright and mounded plant habit.
2. Freely branching habit; dense and full plants.
3. Uniform and freely flowering habit.
4. Daisy-type inflorescences.
5. Pale yellow-colored ray florets with pink-colored apices.
6. Natural season flowering in early October in the Northern Hemisphere.

Plants of the new Chrysanthemum are most similar to plants of the cultivar Stacy. In side-by-side comparisons conducted in Fort Myers, Fla., plants of the new Chrysanthemum differed from plants of the cultivar Stacy in the following characteristics:

1. Plants of the new Chrysanthemum flowered about three to four days earlier than plants of the cultivar Stacy when flowered under artificial daylength conditions.
2. Ray florets of the new Chrysanthemum and the cultivar Stacy differed in color as ray florets of the cultivar Stacy were white with pink apices.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Sweet Yostacy'.

The photograph at the bottom of the sheet comprises a close-up view of typical inflorescences of the cultivar 'Sweet Yostacy'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in an outdoor nursery in Pendleton, S.C., under natural season conditions and practices which approximate those generally used in commercial garden-type Chrysanthemum production. One rooted cutting was planted in a 16.5-cm container in late July, 2002. Plants were not pinched, that is, the terminal apex was not removed to enhance branching. During the production of the plants, day temperatures ranged from 29 to 32° C. and night temperatures ranged from 16 to 21° C. Measurements and numerical values represent averages for typical flowering plants.

Botanical classification: *Chrysanthemum×morifolium* cultivar Sweet Yostacy.

Commercial classification: Daisy-type garden Chrysanthemum.

Parentage: Induced mutation of the *Chrysanthemum×morifolium* cultivar Stacy, disclosed in U.S. Plant Pat. No. 11,852.

Propagation:

*Type.*—Terminal tip cuttings.

*Time to initiate roots.*—About four days at 21° C.

*Time to produce a rooted cutting.*—About ten days at 21° C.

*Root description.*—White, fine and fibrous.

*Rooting habit.*—Freely branching.

Plant description:

*Appearance.*—Perennial herbaceous daisy-type garden Chrysanthemum. Inverted triangle. Stems initially upright, then somewhat outwardly spreading giving a uniformly mounded appearance to the plant. Freely branching with lateral branches forming at every node.

*Plant height.*—About 23 cm.

*Plant diameter.*—About 39 cm.

*Lateral branches.*—Length: About 20 cm. Diameter: About 3.5 mm. Internode length: About 3.2 cm. Aspect: Upright and outwardly spreading. Texture: Pubescent. Color: 146A.

*Foliage description.*—Leaf arrangement: Alternate. Length: About 4.6 cm. Width: About 3.7 cm. Apex: Cuspidate to mucronate. Base: Attenuate with truncate tendencies. Margin: Palmately lobed, sinuses parallel to divergent. Texture: Both surfaces, pubescent; veins prominent on lower surface. Color: Young and mature foliage upper surface: 147A. Young and mature foliage lower surface: 147B. Venation, upper surface: 147A to 147B. Venation, lower surface: 147B. Petiole length: About 7.5 mm. Petiole diameter: About 3.5 mm. Petiole color, both surfaces: Close to 147B.

Inflorescence description:

*Appearance.*—Daisy-type inflorescence form with elongated oblong-shaped ray florets. Inflorescences borne on terminals above foliage, arising from leaf axils. Disk and ray florets arranged acropetally on a capitulum. About 6 inflorescences per lateral.

*Flowering response.*—Under natural season conditions, plants flower in early October in the Northern Hemisphere and continue to flower for at least three weeks depending on weather conditions.

*Inflorescence bud (before showing color).*—Height: About 4 mm. Diameter: About 6 mm. Phyllary color: 143A.

*Inflorescence size.*—Diameter: About 4.3 cm. Depth (height): About 1.3 cm. Disc diameter: About 1.3 cm. Receptacle diameter: About 3.5 mm.

*Ray florets.*—Shape: Elongated oblong. Length: About 2.1 cm. Corolla tube length: About 6.5 mm. Width: About 5 mm. Apex: Mostly emarginate. Margin: Entire. Texture: Smooth, glabrous, satiny. Surface: Mostly flat. Orientation: Initially upright, then about 65° from vertical. Number of ray florets per inflorescence: About 57 in about 2 to 3 rows. Color: When opening, upper surface: 4A to 4B; towards apices, faintly overlain with 53A. When opening, lower surface: 4B to 4C; towards apices, faintly underlain with 53A. Opened inflorescence, upper surface: 8B to 8C; towards apices, overlain with 53A to 59A. Opened inflorescence, lower surface: 8C; towards apices, faintly underlain with 53A to 59A.

*Disc florets.*—Shape: Tubular, apex dentate. Length: About 4.5 mm. Width: Apex: About 1.5 mm. Base: About 1 mm. Number of disc florets per inflorescence: About 110. Color: Immature: 154A to 12A. Mature: Apex: 12A. Mid-section: 154C to 154D. Base: 155D.

*Peduncle.*—Aspect: Flexible, angled about 45° from the stem. Length: First peduncle: About 1.4 cm. Fourth peduncle: About 3.4 cm. Diameter: About 1 mm. Texture: Pubescent. Color: 146A.

*Reproductive organs.*—Androecium: Present on disc florets only. Anther color: 12A. Pollen: Moderate. Pollen color: 15A to 17A. Gynoecium: Present on both ray and disc florets.

*Seed.*—Seed production has not been observed.

Disease/pest resistance: Plants of the new Chrysanthemum have not been shown to be resistant to pathogens and pests common to Chrysanthemums.

Garden performance: Plants of the new Chrysanthemum have been observed to be tolerant to rain, wind and temperatures ranging from 0 to more than 40° C.

It is claimed:

1. A new and distinct cultivar of Chrysanthemum plant named 'Sweet Yostacy', as illustrated and described.

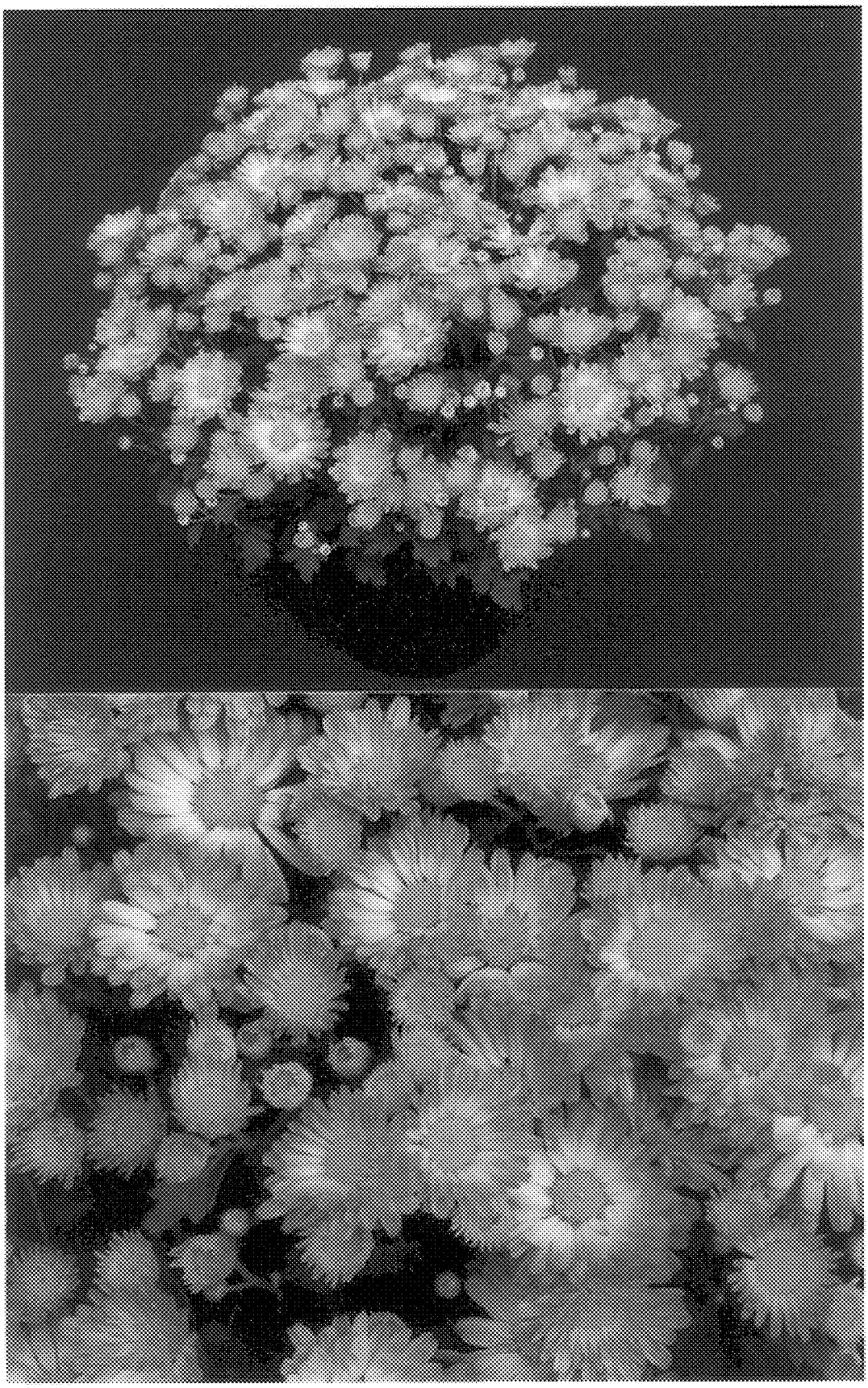

* * * * *